(12) United States Patent
Sarvetnick et al.

(10) Patent No.: US 6,541,251 B1
(45) Date of Patent: Apr. 1, 2003

(54) PANCREATIC PROGENITOR 1 GENE AND ITS USES

(75) Inventors: Nora Sarvetnick, San Diego, CA (US); Howard Fox, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/844,497

(22) Filed: Apr. 26, 2001

Related U.S. Application Data

(60) Provisional application No. 60/199,752, filed on Apr. 26, 2000.

(51) Int. Cl.[7] ........................ C12N 15/85; C07K 14/00; C07K 16/00
(52) U.S. Cl. ..................... 435/325; 530/350; 530/387.1
(58) Field of Search .............................. 435/325, 320.1; 530/350; 536/24.31

(56) References Cited

U.S. PATENT DOCUMENTS 5,663,059 A    9/1997    Hawkins et al.

OTHER PUBLICATIONS

McKinnon et al., Pancreatic duodenal homebox–1, PDX–1, a major regulator of beta cell identity and function, 2001, Diabetologia, vol. 44, pp. 1203–1214.*

Kischstein et al., Report: Stem cells: Scientific progress and future research directions, 2001, NIH, pp. ES–1–ES–10, pp. 23–75.*

Bouwens et al., Transdifferentiation versus stem cell hypothesis for the regeneration of islet beta–cells in the pancreas, 1998, Microscopy Research and Technique, vol. 43, pp. 332–336.*

Bouwens, Luc (1998), "Transdifferentiation Versus Stem Cell Hypothesis for the Regeneration of Islet β–Cells in the Pancreas." *Microscopy Research and Technique*, vol. 43:332–336.

Inoue et al. (1998), "Isolation of Full–Length cDNA of Mouse PAX4 Gene and Identification of Its Human Monologue." *Biochemical & Biophysical Research Communications*, vol. 243:628–633.

Kritzik et al. (1999), "PDX–1 and Msx–2 Expression in the Regenerating and Developing Pancreas." *Journal of Endocrinology*, vol. 163:523–530.

Öberg et al. (1996), "Effects of Certain Growth Factors on In Vitro Maturation of Rat Fetal Islet–Like Structures." *Pancreas*, vol. 12(4):334–339.

St–Ong et al. (1999), "Pancreas Development and Diabetes." *Current Opinion in Genetics and Development*, vol. 9:295–300.

Wang et al. (1995), "Structure of the Human Urokinase Receptor Gene and Its Similarity to CD59 and the Ly–6 Family." *Eur. J. Biochem.* vol. 227:116–122.

* cited by examiner

*Primary Examiner*—James Ketter
*Assistant Examiner*—Celine Qian
(74) *Attorney, Agent, or Firm*—Pamela J. Sherwood; Bozicevic, Field & Francis, LLP

(57) ABSTRACT

Methods for isolating pancreatic progenitor 1 genes are provided. The pancreatic progenitor 1 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

8 Claims, No Drawings

SEQUENCE LISTING

```
<160> NUMBER OF SEQ ID NOS: 5

<210> SEQ ID NO 1
<211> LENGTH: 870
<212> TYPE: DNA
<213> ORGANISM: mus musculus
<220> FEATURE:
<221> NAME/KEY: CDS
<222> LOCATION: (82)...(742)

<400> SEQUENCE: 1
cctttctcta ggtgagattg cttcctctcc agctcaaggc cgtcctttca gaagagcctt        60
cttgtgttca caagcttcac c atg ggc tgg tcc tcc atc ctg aaa agc ctc        111
                        Met Gly Trp Ser Ser Ile Leu Lys Ser Leu
                         1               5                  10 ctc aca gtt ttt gtc ctt agc atc tta gct gtc tgc tct gta gag agt        159
Leu Thr Val Phe Val Leu Ser Ile Leu Ala Val Cys Ser Val Glu Ser
         15                  20                  25
```

```
tac acg tgt ata caa gct acg tgt gaa aat gga aat tgt ctt ggg ggt      207
Tyr Thr Cys Ile Gln Ala Thr Cys Glu Asn Gly Asn Cys Leu Gly Gly
             30                  35                  40 aca agt acc tgt cta acc tct tat agc tgc ttc agc caa ata cag aaa      255
Thr Ser Thr Cys Leu Thr Ser Tyr Ser Cys Phe Ser Gln Ile Gln Lys
     45                  50                  55 ctg gaa aca cca tct cca gat aca aac cta gta ctt gag caa aaa ggg      303
Leu Glu Thr Pro Ser Pro Asp Thr Asn Leu Val Leu Glu Gln Lys Gly
 60                  65                  70 tgt gct tca tat caa aac cta tgt gcc ttg gag ttc tca gca aca ctg      351
Cys Ala Ser Tyr Gln Asn Leu Cys Ala Leu Glu Phe Ser Ala Thr Leu
75                  80                  85                  90 ggg aat cga cag aaa ttt aga tac aag acc cag tgc tgc acc ggt gag      399
Gly Asn Arg Gln Lys Phe Arg Tyr Lys Thr Gln Cys Cys Thr Gly Glu
                 95                 100                 105 cag tgc aac aaa gaa aat ctc act ctg cct cca tta tct tca gaa gtc      447
Gln Cys Asn Lys Glu Asn Leu Thr Leu Pro Pro Leu Ser Ser Glu Val
             110                 115                 120 aat ggt gtt gaa tgt cct gcc tgc tac aat aat aaa acc aat acg tgc      495
Asn Gly Val Glu Cys Pro Ala Cys Tyr Asn Asn Lys Thr Asn Thr Cys
         125                 130                 135 tcc acg aca act ccc cta aag tgc aca ggg gca gag aaa agg tgt att      543
Ser Thr Thr Thr Pro Leu Lys Cys Thr Gly Ala Glu Lys Arg Cys Ile
     140                 145                 150 gag gtt acc agc aga gac cca tct tct aat ata gta atg tat gga aaa      591
Glu Val Thr Ser Arg Asp Pro Ser Ser Asn Ile Val Met Tyr Gly Lys
155                 160                 165                 170 ggc tgt gca aca gaa aat gcc tgt gca ctg tat atg act gtc ttc aat      639
Gly Cys Ala Thr Glu Asn Ala Cys Ala Leu Tyr Met Thr Val Phe Asn
                 175                 180                 185 aac ata caa att aaa acc tcg tgc att tcg acc aat gga agc cct gcc      687
Asn Ile Gln Ile Lys Thr Ser Cys Ile Ser Thr Asn Gly Ser Pro Ala
             190                 195                 200 ctc aaa tcc gct gca tca ctc cca gtt att ctg ctt ctc cag aaa atc      735
Leu Lys Ser Ala Ala Ser Leu Pro Val Ile Leu Leu Leu Gln Lys Ile
         205                 210                 215 ttg ctt t gatcacccag gcaccggcaa tcccacaatc ctgtgtacat aagcccattg    792
Leu Leu
     220 gtatacttgg atgcttattt ccaaaacatg gaacaaataa agactggtga ttacttctct    852 aaaaaaaaaa aaaaaaaa                                                  870

<210> SEQ ID NO 2
<211> LENGTH: 220
<212> TYPE: PRT
<213> ORGANISM: mus musculus

<400> SEQUENCE: 2

Met Gly Trp Ser Ser Ile Leu Lys Ser Leu Leu Thr Val Phe Val Leu
 1               5                  10                  15

Ser Ile Leu Ala Val Cys Ser Val Glu Ser Tyr Thr Cys Ile Gln Ala
             20                  25                  30

Thr Cys Glu Asn Gly Asn Cys Leu Gly Gly Thr Ser Thr Cys Leu Thr
         35                  40                  45

Ser Tyr Ser Cys Phe Ser Gln Ile Gln Lys Leu Glu Thr Pro Ser Pro
     50                  55                  60

Asp Thr Asn Leu Val Leu Glu Gln Lys Gly Cys Ala Ser Tyr Gln Asn
65                  70                  75                  80
```

```
Leu Cys Ala Leu Glu Phe Ser Ala Thr Leu Gly Asn Arg Gln Lys Phe
                85                  90                  95
Arg Tyr Lys Thr Gln Cys Cys Thr Gly Glu Gln Cys Asn Lys Glu Asn
            100                 105                 110
Leu Thr Leu Pro Pro Leu Ser Ser Glu Val Asn Gly Val Glu Cys Pro
        115                 120                 125
Ala Cys Tyr Asn Asn Lys Thr Asn Thr Cys Ser Thr Thr Thr Pro Leu
    130                 135                 140
Lys Cys Thr Gly Ala Glu Lys Arg Cys Ile Glu Val Thr Ser Arg Asp
145                 150                 155                 160
Pro Ser Ser Asn Ile Val Met Tyr Gly Lys Gly Cys Ala Thr Glu Asn
                165                 170                 175
Ala Cys Ala Leu Tyr Met Thr Val Phe Asn Asn Ile Gln Ile Lys Thr
            180                 185                 190
Ser Cys Ile Ser Thr Asn Gly Ser Pro Ala Leu Lys Ser Ala Ala Ser
        195                 200                 205
Leu Pro Val Ile Leu Leu Leu Gln Lys Ile Leu Leu
    210                 215                 220

<210> SEQ ID NO 3
<211> LENGTH: 5524
<212> TYPE: DNA
<213> ORGANISM: mus musculus

<400> SEQUENCE: 3
```

| | | | | |
|---|---|---|---|---|
| gagctcacag tccagtacta gttgcacaac ttgaagctta ttaagctgaa tcaataggga | 60 |
| accataaaat atagtctcca gctatgactt tgaccctggg agatgtgaga gcaggtgtgt | 120 |
| gataggatgg gagtgatggg ggggggggg cccattatga aatgccacaa ggtagcaatg | 180 |
| ccaaattcct tctttggaag gcaagactca agctgactct tgaaaaggc cttcgttgta | 240 |
| tttggtgggg gcaggggtg tacatcatgt tttggctgct gtctcatcat cttgagcaat | 300 |
| tgaacaggaa cggagatagg cttcatcatt agggacccat gatatcttca ctcagcatct | 360 |
| cctgcgagtg tggcaagtct actctcaagc tcatgtttct atgacccggg aaatgttttg | 420 |
| tcaacttact ttgaacaccg gaagttccag ctgagtctct gctggtctct gtaactacag | 480 |
| atgcccttc ttagttggtc ccctctatga ctgttaggtg ttcctcctaa tttcttccac | 540 |
| accccagctt ctgaggcaca tgcacaaccc tgttcctttc ctgtaaccca caccttcttc | 600 |
| aaaactctgc acactgtctt ccctgggagg gggaacttgg cacctgaatt tgaaagaat | 660 |
| gtgttgaaaa tctggatgac tagaggaagt gtgagtcctt ctagcttagc cttttctctcc | 720 |
| actgtaaata agaaggctgc taagctatgc cctaagaaga ggctagccta aaataaata | 780 |
| gacgggctgt gtgtgtgtgt gtgtgtgtgt gtgtgtgtgt gtgtgtgtgt gttagggga | 840 |
| gtgaaattac agagggacac atcaggtccc ttctaagcag agaagttaat agactctagg | 900 |
| gataaaggaa aggatgggag agagaatgac tctgggaatt tgccccaagc aacaatggag | 960 |
| gatggtagct acacactaca ggacaattcc tatacttttt aactttcaag tactctaaac | 1020 |
| tgttctgcgg cttacttcag gcacagcagc attacaaatt ccttcccttc ctttccctac | 1080 |
| caaccagaag ttcaggaaaa actcttctca cagtctctct ctctagatca ggaagtgcag | 1140 |
| tgcacttgac ttcatgccaa gatactattt acagtgtctt aattgccagg cattggtcct | 1200 |
| ctgggctata aaagtgactg ggaggcagag aaagtcctcc tttcatcctt tctctaggtg | 1260 |
| agattgcttc ctctccagct caaggccgtc cttttcagaag agccttcttg gtgagtattt | 1320 |

```
ctagtgtgga ccgtgacacc tggtggtgga ggccatccat taggggggaag gtgacttaga    1380
aagtggtgaa gccatgtcat tagctaaggg tctgattgct cttgagcacc atggcccaga    1440
aatttgtagt acacacagag cctccacctg ttctccagag gagttgtttc ttgactcggc    1500
catgtcaact gtggaagggg atctagtgcc ttccagtccc atgaaagaat tcctcctaat    1560
tgaaagtcct ttcctgggat ccatccccat ccccatgcc tggataaagg atatggagtc    1620
ttttccagtt ttgcatcctt ccaaatggcc acatctagaa aaaccagtgt ttggtaaatt    1680
tgggctttca gaaaggatga gtgaaggggt gattgattga ttgattgatt gattgattga    1740
ttgaatacat ggacaaagaa cacagtctag tatgtggatt gctggattac aggtctgagc    1800
cccattgctc tgatcccatt gttcttactt gcatctcctg cagtgttcac aagcttcacc    1860
atgggctggt cctccatcct gaaaagcctc ctcacagttt ttgtccttag catcttagct    1920
gtctgctctg taggtaagag taaacaaagc aacgtaaagg ggaggtaagc agtcacgtgc    1980
ctggggggagg tagccaaccc catgagactc cagtagtctg tttatcctcc catggcttct    2040
tgactcagaa gcaacatcca ctacaaggct ttgggattcc cctttaaatg atgtgcattt    2100
cctccttaca gagagttaca cgtgtataca agctacgtgt gaaatggaa attgtcttgg    2160
gggtacacgt acctgtccaa cctcttatag ctgcttcagc caaatacaga aactggaaac    2220
accatgtaag ccaaccctcg ctaccttgag catcctccaa ttcatccttg cctcctttcc    2280
aggatgagac taggagctgg gtggagatgg agcatgtgct tgctgtaggc cctagactct    2340
acatgatcag gaccatttgg gagtgactgc actcttttag tgtgtcaggg atcaaactca    2400
gggcatcatg cttgctaagt gagtacctta ccactagtca ctccctttgt agcaagtggt    2460
ccatgctctg ttggtttgtt ctcgagagac tagtgcagag agactcgaga aagtacaaca    2520
ctcaagatag agggggatgaa ggaacagatt atttaccact agcttaggag gaaaatttac    2580
ttggtggttc aatttcctgc agctccagat acaaacctag tacttgagca aaaagggtgt    2640
gcttcatatc aaaacctatg tgccttggag ttctcagcaa cactgggggaa tcgacagaaa    2700
tttagataca agacccagtg ctgcactggt gagcagtgca acaaagaaaa tctcactcgt    2760
gagtataccc cctgtctgtg tcccaacaca taaacacagt tagggtctgt gccccaccac    2820
ctacctgctc agggttcctc tatcttccat gggtctatct ctgtgcttat gggcagcagc    2880
agtgatgcct atccttccca tttcgcttga cacctttatt tgtaagggcc tgggttggat    2940
ataagccctg ctcttgagat atgtgtgcac acacttgcgt ttgcagactg agaaacagcg    3000
aggcagcaga aattggtccg gggtctactc tctaagtagg ttcagtgaat ctataggttt    3060
aagtgctctg ctctgctctc tcctctctct gctctgctct ctctgctctg ctctgctctc    3120
tctgctctgc tctgctctct gctctctgct ctctgctctc tgctctctgc tctctgctct    3180
ctgctctctg ctctctgctc tctgctctct gctctctgct ctctgctctc tgctctctgc    3240
tctctgctct ctgctctgct ctgctctctg ctttctctg ctttctctg ctctgctctc    3300
tgctctgctc tctgctctct ctgccctgct ctactctgct ctctgctctc tgctctctct    3360
gctctgatcg ctctctctgc tctgctctct ctgctctgat ctgctctctc tctctgctct    3420
ctctgctctg ctctttctgc tctgctctct ctgctcctcc tgtgaagaga ctttcctcat    3480
ctacttcatt actcatcttg gattttgtat tgttgaaatg gagtcttgct atgcatccag    3540
gcttgcatta tattactggg atgaagtaat cctcctgcct cagccaccaa agttggagta    3600
gctgggagca caggtctgtg tggaccacaa cttggtcatc tctcactctt tgaacagcat    3660
```

-continued

```
acttttagaa aacagatcct ctcctctccc attatctagg actttcctc caaggcaaag      3720 agtagagtaa ctgatgaaag tgaggacaac tctgaattcc catgaggtcc tacctggcac      3780
tcacacccca gtgccttctc ctgagcctcc tcccagctca tcctcactgc aacgcttttt      3840
ggtagaatcg tggaaaaacc ctgtattaga ggagcagtag atagacatat tctcagctgt      3900
ttcttctttc tatttcccaa gatgaaaacg ttttctctc cattcagtgc ctccattatc       3960
ttcagaagtc aatggtgttg aatgtcctgc ctgctacaat aataaaacca atacgtgctc      4020
cacgacaact cccctaaagt gcacaggggc agagaaaagg tgtattgagg ttaccagcag      4080
aggtatgagt gtattattat tattattatt attattatta ttattattat tattattatt      4140
attgcttgtt actttaaaat gtggatggtc tgtgtatcca aagcttagca gctaaaaagt      4200
agcaaatatg aatcccagtt tttgcaggtc tagaatctga gcatgtcact ggcactggtt      4260
gtggctcagg gtgtctccta ggactgtgtg agctgtcagc aggagctgag gtccttcata      4320
tgctcagggt gtcctgggg gcagtgtgat tgtcatcag ggtctggggt ccttcatatg        4380
ctcagggtgt cttctgggc tgtgtgactt gtcagcaggg cctgaggtcc ttcagatatg       4440
ggatctgctt tccacttcct tcatggtttg gtattgtcag ctccttttca tgaagtggcc      4500
ccatggtcta tcagctgact tccctcggta ctagtgatca gatagagaga ggcagactga      4560
taggaggagc tataggcttt aatagtctaa tctcagaagt gacatcattt ctgctcctgt      4620 ttttgtatt tttttttaaa ttaaaacttc aaagaactta caaatttaaa acctcatagc       4680
gtgagaatat tcagacccaa agatcatcca tctccaatct gaagaagtgg agaatgggat     4740
tgaattttac actttcattg tcaactatag ttttatgcgc ttgtcctcca tataagtata     4800
tgcacacaca cagagagaca caacaagcaa gcaaacaaca aaaacaaaat ccagggcaga     4860
atcaaaacta agaatgcaat tagttcctaa ttctctcagt cttgcgtgtc caccccatct     4920
ttccgcatca cctaatgtga cagacccctc tcaagagtca aatctctccc ctcatctcta     4980
ctctcaatac aatccttata cagtgaatcc tgatacaaca tgaatggggc ctacagaaaa     5040
ccacttggcc agaagttgga gagtggggga ggggtcctct tagaaattag tttcctcaca     5100
gagaaaaggg caaggtaggg ccaagcaagc tcttatctct ccaagatcta gagggagtca     5160
tttgctgaca gttgaagagg tgtgtgtgtg tgtgtgtgtg tgtgtgtgtg tgtgtgtgtg     5220
tgttggatgt agggggtagt aagggaaaga aatacaaatg cttgcacctg ccttgctgtg     5280
atatcctgca atgggccctt agctcattga caacacagca ggtgacttca tttctggatg     5340
tcacataggt gagcacttga gcttttcata gaccgctgtg aatttagtga aagttttatg     5400 attttttttcc ctgaatgatc agaacaatgt attgttgtgt agggtgcata tatcactcag    5460
gtaggagcca gaaaagcaac tgtgggatcg agtcgacgcc ctatagtgag tcgtattaga     5520
gctc                                                                   5524
```

```
<210> SEQ ID NO 4
<211> LENGTH: 20
<212> TYPE: DNA
<213> ORGANISM: mus musculus

<400> SEQUENCE: 4 gccgtcctttt cagaagagcc                                                    20

<210> SEQ ID NO 5
<211> LENGTH: 19
<212> TYPE: DNA
<213> ORGANISM: Mus musculus
```

```
<400> SEQUENCE: 5
caggattgtg ggattgccg                                              19
```

PANCREATIC PROGENITOR 1 GENE AND ITS USES

BACKGROUND OF THE INVENTION

There are 15.7 million people in the United States who have diabetes, which is the seventh leading cause of death in this country. As a chronic disease that has no cure, diabetes is one of the most costly health problems in America.

Health care and other costs directly related to diabetes treatment, as well as the costs of lost productivity, run $92 billion annually.

Type I autoimmune diabetes results from the destruction of insulin producing beta cells in the pancreatic islets of Langerhans. The adult pancreas has very limited regenerative potential, and so these islets are not replaced after they are destroyed. The patient's survival then depends on exogenous administration of insulin. There are an estimated 500,000 to 1 million people with type 1 diabetes in the United States today. The risk of developing type 1 diabetes is higher than virtually all other severe chronic diseases of childhood.

The pancreas is composed of at least three types of differentiated tissue: the hormone-producing cells in islets (4 different cell types), the exocrine zymogen-containing acini, and the centroacinar cells, ductules and ducts (ductal tree). All of these cells appear to have a common origin during embryogenesis in the form of duct-like protodifferentiated cells. Later in life, the acinar and ductal cells retain a significant proliferative capacity that can ensure cell renewal and growth, whereas the islet cells become mitotically inactive.

During embryonic development, and probably later in life, pancreatic islets of Langerhans originate from differentiating epithelial stem cells. These stem cells are situated in the pancreatic ducts but are otherwise poorly characterized.

Pancreatic islets contain four islet cell types: alpha, beta, delta and pancreatic polypeptide cells that synthesize glucagon, insulin, somatostatin and pancreatic polypeptide, respectively. The early progenitor cells to the pancreatic islets are multipotential and coactivate all the islet-specific genes from the time they first appear. As development proceeds, expression of islet-specific hormones becomes restricted to the pattern of expression characteristic of mature islet cells.

The characterization of pre-islet cells is of great interest for the development of therapeutics to treat diseases of the pancreas, particularly IDDM. Model systems have been described that permit the study of these cells. For example, Gu and Sarvetnick (1993) *Development* 118:33–46 identify a model system for the study of pancreatic islet development and regeneration. Transgenic mice carrying the mouse γ-interferon gene linked to the human insulin promoter exhibit inflammatory-induced islet loss. Significant duct cell proliferation occurs in these mice, leading to a striking expansion of pancreatic ducts. Endocrine progenitor cells are localized in these ducts. This model provides a source of progenitor cells for further study.

The differential expression of genes by progenitor cells, as compared to their differentiated progeny, is of interest for the characterization and isolation of the progenitor cells. Where the differentially expressed genes encode a receptor for biologically active molecules, the marker may further provide information about factors that affect the growth or differentiation of the progenitor cells. Where such genes encode proteins such as transcription factors, the marker may provide information about regulated gene expression in the progenitor cells.

Relevant Literature

Kritzik et al. (1999) *J Endocrinol* 163(3):523–30 found that PDX-1, a transcription factor required for insulin gene transcription as well as for pancreatic development during embryogenesis, is expressed in the duct cells of IFNγ mice. Also demonstrated was elevated expression of the homeobox-containing protein Msx-2 in the pancreata of fetal mice as well as in adult IFNγ mice, identifying this molecule as a marker associated with pancreatic development and regeneration.

Oberg-Welsh and Welsh (1996) *Pancreas* 12:334–339 study the expression of protein tyrosine kinases in different preparations of insulin producing cells by polymerase chain reaction (PCR). Among the tyrosine kinases were the fibroblast growth factor receptor-4 (FGFR-4), c-kit, the insulin-like growth factor (IGF-1) receptor, and the cytoplasmic tyrosine kinase Jak2, which associates with the activated receptor for growth hormone (GH).

Inoue et al. (1998) *Biochem Biophys Res Commun* 243(2):628–33 isolated a full-length cDNA of mouse PAX4 gene and a human homolog. Studies have suggested that PAX4, a member of the paired box (PAX) gene family, is involved in the mechanism regulating the fate of pancreatic islet endocrine progenitor cells.

Bouwens (1998) *Microsc Res Tech* 43(4):332–6 review the question whether islet beta-cell regeneration or neogenesis in the pancreas depends on "embryonic-like" stem cells or on transdifferentiation of "fully differentiated" cells.

St-Onge et al. (1999) Curr Opin Genet Dev 9(3):295–300 reviews the role of transcription factors such as Pdx1, p48 and Nkx2.2 pancreas development, including the role of Sonic Hedgehog.

The uPAR/CD59/Ly-6/snake toxin family is a group of proteins characterized by cysteine-rich consensus signature motifs, as well as conserved tertiary structures and genomic organization. Wang et al. (1995) *Eur J Biochem* 227(1–2):116–22 compares the exon organization of the uPAR gene with that of human CD59 and murine Ly-6.

SUMMARY OF THE INVENTION

Isolated nucleotide compositions and sequences are provided for pancreatic progenitor 1 (PP1) genes. The PP1 nucleic acid compositions find use in identifying homologous or related genes; in producing compositions that modulate the expression or function of its encoded protein, PP1; for gene therapy; mapping functional regions of the protein; and in studying associated physiological pathways. In addition, modulation of the gene activity in vivo is used for prophylactic and therapeutic purposes.

In one embodiment of the invention, antibodies specific for the PP1 protein are used in the identification and isolation of cells expressing PP1, e.g. pancreatic progenitor cells. In a related embodiment, compositions of PP1 positive cells are provided.

DESCRIPTION OF THE SPECIFIC EMBODIMENTS

Nucleic acid compositions encoding pancreatic progenitor 1 (PP1) are provided. They are used in identifying homologous or related genes; in producing compositions that modulate the expression or function of its encoded protein; for gene therapy; mapping functional regions of the protein; and in studying associated physiological pathways. Antibodies that recognize PP1 are useful in the identification and isolation of cells expressing PP1, particularly pancreatic progenitor cells.

Characterization of PP1

PP1 encodes 221 a amino acid protein containing two cysteine-rich domains. Sequence analysis demonstrates that PP1 is a member of the uPAR/CD59/Ly-6/snake toxin family. PP1 is expressed in the ducts of the regenerating pancreas in regions where new islets are developing. In addition, PP1 is expressed in embryonic foregut, stomach and duodenum, but not in developing pancreas or mature pancreas, demonstrating that PP1 is a marker of progenitor or stem cells. The PP1 expressing cells in the gut are localized in the endodermal pouch; and is also found in intestinal crypt cells. These results indicate that PP1 is a progenitor or stem cell marker in multiple lineages.

The nucleotide sequence of mouse PP1 is provided as SEQ ID NO:1; and the amino acid sequence of the encoded polypeptide as SEQ ID NO:2. The genomic sequence, including the promoter region, is provided as SEQ ID NO:3.

Homologs of PP1 are identified by any of a number of methods. For example, a fragment of the cDNA may be used as a hybridization probe against a cDNA library from the target organism of interest, where low stringency conditions are used. The probe may be a large fragment, or one or more short degenerate primers. Such sequences are selected from regions that are not likely to diverge over evolutionary time and are of low degeneracy. The complementary binding sequence may be at least 14 nucleotides, preferably at least about 17 nucleotides and usually at least about 50 nucleotides. Conveniently, amplification reactions are used to generate an initial probe, which can then be used to hybridize to a library; for rapid amplification of cloned ends (RACE); etc. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence. The source of mRNA for a cDNA library may use cells where PP1 is known to be expressed, for example pancreatic progenitor cells.

Nucleic acids having sequence similarity to the provided PP1 genetic sequences are detected by hybridization under low stringency conditions, for example, at 50° C. and 6×SSC (0.9 M NaCl/0.09 M Na citrate) and remain bound when subjected to washing at 55° C. in 1×SSC (0.15 M NaCl/0.015 M Na citrate). Sequence identity may be determined by hybridization under stringent conditions, for example, at 50° C. or higher and 0.1×SSC (15 mM NaCl/01.5 mM Na citrate). Nucleic acids having a region of substantial identity to the provided PP1 sequences, e.g. allelic variants, genetically altered versions of the gene, etc., bind to the provided PP1 sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between species in a group, e.g. human and mouse, homologs have substantial sequence similarity, i.e. at least 75% sequence identity between nucleotide sequences, in some cases 80 or 90% sequence identity, and may be as high as 95% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), J. Mol. Biol. 215:403–10. In general, variants of the invention have a sequence identity greater than at least about 65%, preferably at least about 75%, more preferably at least about 85%, and may be greater than at least about 90% or more.

PP1 Nucleic Acid Compositions

Nucleic acids encoding PP1 may be cDNA or genomic DNA or a fragment thereof. The term "PP1 gene" shall be intended to mean the open reading frame encoding specific PP1 polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a PP1 protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where PP1 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res* 6: 327–33; and Joulin and Richard-Foy (1995) *Eur J Biochem* 232: 620–626.

The regulatory sequences may be used to identify cis acting sequences required for transcriptional or translational regulation of PP1 expression, especially in different tissues or stages of development, and to identify cis acting sequences and trans acting factors that regulate or mediate PP1 expression. Such transcription or translational control regions may be operably linked to a PP1 gene in order to promote expression of wild type or altered PP1 or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening probes, etc. Larger DNA fragments, i.e. greater than 100 or 250 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The PP1 genes are isolated and obtained in substantial purity, generally as other than an intact, naturally occurring chromosome. Usually, the DNA will be obtained substantially free of other nucleic acid sequences that do not include a PP1 sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of PP1 gene expression in the sample.

The sequence of a PP1 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989). Such mutated genes may be used to study structure-function relationships of PP1, or to alter properties of the protein that affect its function or regulation.

PP1 Polypeptides

The subject gene may be employed for producing all or portions of PP1 polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a PP1 gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the PP1 gene in eukaryotic cells, where the PP1 protein will benefit from native folding and post-translational modifications. Small peptides can also be synthesized in the laboratory. Peptides that are subsets of the complete PP1 sequence, e.g. peptides of at least about 8 amino acids in length, usually at least about 12 amino acids in length, and may be as many as about 20 amino acids in length, up to substantially the length of the intact protein, may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed PP1 polypeptides are used for the production of antibodies, where short fragments provide for antibodies specific for the particular polypeptide, and larger fragments or the entire protein allow for the production of antibodies over the surface of the polypeptide. Antibodies may be raised to the wild-type or variant forms of PP1. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

PP1 Expressing Cells

PP1 binding reagents, e.g. antibodies, are useful for the identification or enrichment of PP1 positive cells from complex cell mixtures. Such cell populations are useful in transplantation, for experimental evaluation, and as a source of lineage and cell specific products, including mRNA species useful in identifying genes specifically expressed in these cells, and as targets for the discovery of factors or molecules that can affect them.

The PP1 positive pancreatic progenitor cell population is useful in transplantation to provide a recipient with pancreatic islet cells, including insulin producing beta cells; for drug screening; experimental models of islet differentiation and interaction with other cell types; in vitro screening assays to define growth and differentiation factors, and to additionally characterize genes involved in islet development and regulation; and the like. The native cells may be used for these purposes, or they may be genetically modified to provide altered capabilities.

Cells from a regenerating pancreas, from embryonic foregut, stomach and duodenum, or other sources of pancreatic progenitor cells may be used as a starting population. The progenitor cells may be obtained from any mammalian species, e.g. equine, bovine, porcine, canine, feline, rodent, e.g. mice, rats, hamster, primate, etc., particularly human. The tissue may be obtained by biopsy from a live donor, or obtained from a dead or dying donor within about 48 hours of death, or freshly frozen tissue, tissue frozen within about 12 hours of death and maintained at below about $-20°$ C., usually at about liquid nitrogen temperature ($-180°$ C.) indefinitely. The number of cells in a sample will generally be at least about $10^3$, usually at least $10^4$, and may be about $10^5$ or more. The cells may be dissociated, in the case of solid tissues, or tissue sections may be analyzed. A tissue source of interest for investigative purposes is the transgenic mouse described by Gu and Sarvetnick (1993) *Development* 118:3346.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent analysis or sorting for each marker.

The subject PP1 cell populations may be separated from other cells, e.g. differentiated islet and duct cells, on the basis of PP1 expression, which is identified with affinity reagents, e.g. monoclonal antibodies. The separation may also use negative markers to exclude differentiated epithelial or islet cells.

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5–25 mM. Convenient buffers include HEPES, phosphate buffers, lactate buffers, etc.

Separation of the subject cell populations will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The labeled cells are then separated as to the expression of PP1. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5–10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. The specific culture conditions are chosen to achieve a particular purpose, i.e. differentiation into insulin producing cell populations, maintenance of progenitor cell activity, etc.

The PP1 positive cells may be used in a wide variety of ways. The progenitor cells may be used in conjunction with the culture system in the isolation and evaluation of factors associated with the differentiation and maturation of islet cells. Thus, the progenitor cells may be used in assays to determine the activity of media, such as conditioned media, evaluate fluids for growth factor activity, involvement with dedication of lineages, or the like.

The PP1 progenitor cell populations may be used for reconstitution of islet cell function in a recipient, e.g. insulin producing beta cells, glucagon producing cells, etc. The condition may be caused by genetic or environmental conditions, e.g. autoimmune diseases, type I diabetes mellitus, etc. Autologous cells or allogeneic cells, may be used for progenitor cell isolation and subsequent transplantation.

Diagnostic Uses

The subject nucleic acid and/or polypeptide compositions may be used to analyze a patient sample for the expression of PP1, or variants thereof. For example, biochemical studies may be performed to determine whether a sequence polymorphism in a PP1 coding region or control regions is associated with disease. Disease associated polymorphisms may include mutations that alter expression level, that affect protein function, etc.

Changes in the promoter or enhancer sequence that may affect expression levels of PP1 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express PP1 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual,* CSH Press 1989, pp.14.2B14.33. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type PP1 sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in PP1 may be based on the functional or antigenic characteristics of the protein. Protein truncation assays are useful in detecting deletions that may affect the biological activity of the protein. Various immunoassays designed to detect polymorphisms in PP1 proteins may be used in screening. Where many diverse genetic mutations lead to a particular disease phenotype, functional protein assays have proven to be effective screening tools.

Antibodies specific for a PP1 polypeptide may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal PP1 in cells. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Modulation of Gene Expression

The PP1 genes, gene fragments, or the encoded protein or protein fragments are useful in gene therapy to treat disorders associated with PP1 defects. Expression vectors may be used to introduce the PP1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or PP1 protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the PP1 protein or DNA, then bombarded into skin cells.

Antisense molecules can be used to down-regulate expression of PP1 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. As an alternative to anti-sense inhibitors, catalytic nucleic acid compounds, e.g. ribozymes, anti-sense conjugates, etc. may be used to inhibit gene expression.

Genetically Altered Cell or Animal Models for Pancreatic Progenitor 1 Function The subject nucleic acids can be used to generate transgenic animals or site specific gene modifications in cell lines. Transgenic animals may be made through homologous recombination, where the normal PP1 locus is altered. Alternatively, a nucleic acid construct is randomly integrated into the genome. Vectors for stable integration include plasmids, retroviruses and other animal viruses, YACs, and the like.

The modified cells or animals are useful in the study of PP1 function and regulation. For example, a series of small deletions and/or substitutions may be made in the PP1 gene to determine the role of the cysteine rich domains, functions in pancreatic differentiation, etc. Specific constructs of interest include anti-sense PP1, which will block PP1 expression, or expression of dominant negative PP1 mutations. A detectable marker, such as lac Z may be introduced into the PP1 locus, where upregulation of PP1 expression will result in an easily detected change in phenotype.

One may also provide for expression of the PP1 gene or variants thereof in cells or tissues where it is not normally expressed or at abnormal times of development. In addition, by providing expression of PP1 protein in cells in which it is not normally produced, one can induce changes in cell behavior.

DNA constructs for homologous recombination will comprise at least a portion of the PP1 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keyed et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc.

In Vitro Models for Pancreatic Progenitor 1 Function

Drug screening may be performed using an in vitro model, a genetically altered cell or animal, or purified PP1 protein. One can identify ligands or substrates that bind to, modulate or mimic the action of PP1.

Drug screening identifies agents that provide a replacement for PP1 function in abnormal cells. Of particular interest are screening assays for agents that have a low toxicity for mammalian cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of pancreatic progenitor 1. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of developmental abnormalities attributable to a defect in PP1 function, etc., in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–100 wt. %.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

A novel cDNA, pancreas progenitor 1 (PP1) is isolated from the INF-γ induced regenerating pancreas. PP1 is a new member of the urokinase plasmigogen activator (uPAR)/CD59/Ly-6/snake toxin family. This gene is expressed specifically in the duct of the regenerating pancreas, particularly in the regions of endocrine cell differentiation, but not in the normal pancreas. During embryonic organogenesis, PP1 is expressed in foregut, the region from which pancreas develops. These results demonstrate that PP1-positive cells represent pancreatic progenitors that possess the differential potential to regenerate pancreatic islets.

Methods:

RNA isolation: Pancreas total RNA was purified from tissues from wild type-NOD scid mice, IFNγ transgenic NOD scid mice and IL-4 transgenic NOD scid mice, respectively. Briefly, frozen tissues were mechanically homogenized in solution D (4 M guanidinium thiocyanate, 25 mM sodium citrate, pH 7.0; 0.5% sarcosyl, 0.1 M 2-mercaptoethanol) and pass through a 18–21 gauge needle at least 3 times to shear the genomic DNA. 0.1 volume 2 M NaOAc (pH 4.0), 1 volume acid-phenol, and 0.2 volume chloroform were sequentially added and samples were vortexed after each addition. The samples were placed on ice for 15 min. and centrifuged at 10,000 rpm at 4° C. for 15 min. Aqueous phase was mixed with equal volume isopropanol, vortexed and incubated at −20° C. for 1 hour. Samples were centrifuged again at 10,000 rpm for 15 min. at 4° C. to pellet precipitated RNA. The RNA pellets were re-dissolved in 500 µl Solution D, and 500 µl isopropanol added to re-precipitate the RNA. The RNA was recovered by microcentrifugation, and washed with 70% ethanol. The RNA was dissolved in 0.1% SDS, 1 mM EDTA (pH 8.0) and stored at −20° C.

PolyA$^+$ RNAs for subtractive hybridization experiments were isolated from wild type and IFNγ transgenic NOD scid mice by using Micro-FastTrack™ kit (Invitrogen). Briefly, samples were lysed, protease treated, and bound to oligo (dT) cellulose. The oligo (dT) cellulose was washed by sequential pelleting and resuspension in the binding buffer at least 4 times, and non-poly A$^+$ RNA removed with a low salt wash. The poly A$^+$ RNA was then eluted, precipitated, and resuspended in 10 mM Tris, pH 7.5.

Subtractive hybridization of pancreatic cDNA: Using PCR Select cDNA Subtraction Kit (Clontech, Palo Alto, Calif.), the subtractive hybridization experiment was performed. Driver and tester cDNAs were synthesized from PolyA$^+$ RNAs from wild type and IFNγ transgenic NOD scid mice, respectively. Each of two portions of tester cDNA were ligated with a different adapter sequence. Two sets of adapter-ligated cDNA were first hybridized to driver cDNA. In second hybridization, the two primary bridization samples were mixed and again subjected to hybridization with driver cDNA. The new hybrid molecules containing different adapters, which correspond to differentially expressed cDNAs, were used as templates and subjected to PCR, using primers specific to the adapters, to amplify the desired cDNAs. In the first PCR, "touchdown PCR" was used at annealing temperature from 69° C. to 60° C. with a MiniCycler (MJ Research, Watertown, Mass.), then continued at 62° C. for 18 cycles. Second PCR was performed at 94° C., 15 seconds; 68° C., 2.5 minutes for 14 cycle. The amplified cDNA molecules were separated by agarose gel electrophoresis. Different molecular size pools of cDNA were purified from gel, ligated into the PCR2.1 vector (In Vitrogen), and transformed into bacteria.

Northern blot analysis: Multiple mouse tissue northern blot (MTN) and Embryo northern blot were purchased from CLONTECH (Palo Alto, Calif.). For blots containing total RNA from pancreas, Northern blotting was carried out essentially as described by Sambrook et al. (1989). 15 Fg total RNA were electrophoresed on a 1% agarose containing 6% formaldehyde and transferred onto Zeta-probe Blotting Membranes (Bio-Rad) in 10×SSC. The cDNA insert from the PP1 clone was randomly labeled with á-$^{32}$P-dCTP, purified by Sephadex G-50 chromatography, and applied to the blots in a concentration of 1–2 H $10^6$ cpm/ml in Express Hybridization Buffer (Clontech, Palo Alto, Calif.). Blots were hybridized at 68° C. for 1 hour, then washed at a final stringency of 0.1×SSC, 50° C., and exposed to film. The relative size of the resulting signals was estimated by comparison to the migration of RNA markers (Ambion) and the migration of the 18S and 28S RNAs revealed by Radiant Red RNA Gel Stain (Bio-Rad).

RT-PCR for 5" and 3" regions of PP1 mRNA: 1 µg mRNA isolated from IFN-γ transgenic pancreas was first treated with DNAse (Promaga) and RNAse inhibitor (Promega) at 37° C. for 30 minutes. Enzymes were inactivated by 10% SDS and 0.5 M EDTA. mRNA was purified with RNA phenol and chloroform and precipitated with Na Acetate (3 M, pH 5.2) and ethanol. mRNA sample was reverse-transcribed using oligo-dT with MMLV Reverse transcriptase (Clontech RT-PCR Kit) at 42° C. for 1 hour. Appropriate volume of cDNA was amplified with primers corresponding to PP1 sequence (primers: (SEQ ID NO:4) GCCGTCCTTTCAGAAGAGCC and (SEQ ID NO:5) CAGGATTGTGGGATTGCCG). PCR cycle was performed at 94° C., 30 seconds (1×); 93° C., 15 seconds; 60° C., 30 seconds; 72° C., 50 seconds (30×); 75° C., 5 minutes with a MiniCycler (MJ Research). DNA was purified from gel and cloned into pCR 2.1 vector for cDNA sequence analysis.

Library Screening and Cloning of PP1. Mouse genomic library from 129 genomic DNA was used to screen for the PP1 gene. Briefly, recombinant bacteriophages were used to infect XL-blue MRA host cells (Stratagene, La Jolla, Calif.) in 0.6% top agar. Cells were grown in LB plates at 37° C. until plaques grew up to 1 mm in diameter. Plaques were lifted to a nylon membrane (Du Pont), and were subsequently denatured in 0.5 M NaOH for 2 minutes, neutralized in 1.0 M Tris-HCl (pH 7.5) for 2 minutes and baked at 80° C. for 30 minutes. PP1 cDNA was labeled with [γ-P$^{32}$] dCTP Amersham) by the random-priming method. Membranes were hybridized and washed as described above. Positive plaques were picked up and incubated in SM buffer for next screening. Secondary screening was performed in same method. Individual bacteriophages containing PP1-hybridizing DNA was amplified and isolated with method described by Sambrook et al., supra. Briefly, positive bacteriophages were grown up in NZY agarose plates until the plaques covered the entire surface of plate, and eluted with diluent buffer (10 mM Tris.Cl pH. 7.5, 10 mM MgSO$_4$). The supernatant was collected and treated with DNAase I. Bacteriophage particles were recovered by centrifugation following 10% SDS treatment for 5 minutes at 68° C. Bacteriophage DNA were purified by extracting with phenol and chloroform, and precipitating with isopropanol. DNA fragments containing the PP1 were analyzed by restriction enzymes and a selected fragment subcloned into pBluescript SK(+) for sequence analysis.

Sequence Analysis. Double-stranded plasmid clones were sequenced by primer-directed dideoxy chain termination method with dye-labeled terminators using the Prism Terminator Kit (Applied Biosystems) with DNA Sequencer Model 373A (Applied Biosystems) by the TSRI microchemistry Core facility. The sequencing primers used were forward, reverse and synthetic oligos based on sequences already obtained. DNA and protein sequence were analyzed using the MacVector 6.0 software (Oxford Molecular Group).

Cell transfection and polyclonal antibody production: To produce polyclonal antibody against PP1 protein, cell transfection was performed. A fragment of PP1 cDNA was cloned into pLNCX retroviral vector (Clontech) at Hind III and Hpa I site. At 80% confluence, PT67 packaging cells were infected with 1 µg of recombinant viral cDNA per ml medium in 11 mM calcium phosphate for 12 hours at CO$_2$ incubator. Transfected cells were selected with 500 µg G418 (Gibco) per ml DMEM-F12 plus 10% fetal calf serum for at least 12 days until all non-transfected cells died. The medium containing recombinant virus was harvested and used to infect SIRC (from ATCC) target cells, rabbit cornea cells for over night. SIRC cells were fed with DMEM plus 10% serum under treatment of G418 (400 µg/ml) for more than 14 day. Normal SIRC were cultured without G418. For immunizing the rabbits, transfected SIRC were changed to medium containing 2% rabbit serum instead of fetal calf serum one day before injection of cells to rabbits. Two rabbits were immunized with 20×10⁶ cell for each rabbit and boosted with same number of cells every 3 weeks. After the fifth boost, sera were collected from both rabbits. To remove antibodies reacting against normal SIRC cells, 100 µl of antiserum was mixed with 40×10⁶ normal SIRC and incubated on ice for 2 hours to adsorb such antibodies. Antiserum was separated from cells by centrifuging and collected for immunohistochemistry analysis.

Immunohistochemistry staining: Carnoy's or Bouin's fixed tissues from normal mice and IFNγ transgenic mice were embedded in paraffin and sectioned at 5 µm. After dewaxing and rehydrating, endogenous peroxidases were blocked by reacting with 3% $H_2O_2$ in methanol for 30 minutes. Sections were rinsed in PBS for 3 times and blocked in 0.5% casein in PBS for 30 minutes. Sections were stained with primary antibody (1:800 dilution) for over night at 4° C. In negative control sections, primary antibody was replaced by 5% casein buffer. After washing in PBS, sections were sequentially incubated with biotinylated goat anti-rabbit IgG antibody (Vector) and diluted to 1:300 for 1 hour at room temperature, streptavidin-peroxidase (Zymed) in 1:5 dilution in PBS for 30 minutes. Peroxidase activity was visualized by applying VIP substrate kit (Vector) for 3–15 minutes. Sections were counterstained with methyl green for Carnoy's fixing or with hematoxylin for Bouin's fixing.

In situ hybridization. Mouse tissues including pancreas, stomach, intestine from IFN-γ transgenic mice, and mouse embryos (15 and 16 day old) were examined. Tissues were immersion-fixed for 24 hours in 4% freshly-prepared paraformaldehyde at 4° C., and embedded in paraffin. Sections (5 Em) were dewaxed, hydrated and protease-treated (20 µg/ml). The PP1 cDNA was transferred to the pBluescript SK(+) vector and linearized with restriction enzymes. $^{35}$S-UTP labeled antisense and sense probes were produced with T7 and T3 RNA polymerase. Sections were prehybridized in hybridization buffer (50% formamide, 0.3 M NaCl, 20 mM Tris pH 8.0,5 mM EDTA, 10 mM DTT, 10% dextran sulfate and 1×Denhardt's solution) for at least 1 hour at 42° C., followed by hybridization at 42° C. in hybridization buffer containing 3×10⁶ cpm of probe per 200 µl. Sections were rinsed, treated with 20 µg/ml RNAse A, washed to a final stringency of 0.2×SSC, 42° C., then dried. Slides were exposed to Kodak NTB2 liquid emulsion for autoradiography for 1–3 weeks, and developed. Sections were subsequently counterstained with hematoxylin and eosin.

Results:

Screening the genes regarding pancreatic regeneration: Pancreatic regeneration occurs in IFN-γ transgenic mice but not in normal mice. To investigate the molecular mechanism of pancreatic regeneration in this transgenic mouse model, we decided to screen for genes that are potentially involved in the pancreatic regeneration. Using a subtractive hybridization technique, the cDNA library was constructed from differentially expressed pancreas cDNA. From this cDNA library, 80 clones were partially sequenced and resulted sequences were compared with GeneBank database. Unique novel clones were further analyzed by Northern blot. In this Northern analysis, IL-4 transgenic pancreas was used as control as well as non-transgenic pancreas since some hallmarks of cytokine stimulation, such as fibrosis, are shared between two strains of transgenic mouse. The clones that expressed only in INF-γ transgenic pancreas were selected as candidates for continuing analysis. Among these clones, four clones appeared to be potentially related to pancreatic regeneration by primary sequencing and Northern blot analyses, one of which has been named herein as pancreatic progenitor 1 (PP1).

Sequence analysis of PP1: To characterize the structure of the PP1 gene, it was molecularly cloned by RT-PCR. The entire sequence of PP1 cDNA was obtained by primer-walking. Sequence analysis revealed that this cDNA was not identical to other genes in GenBank database and has an open reading frame (ORF) encoding a predicted 221 amino acid protein. This amino acid sequence contains 20 cysteines. Searching for protein homologies revealed that PP1 is a homologue to urokinase plasminogen activator (uPAR)/CD59/Ly-6/snake toxin family. The uPAR/CD59/Ly-6/snake toxin family is characterized by cysteine-domains. Each putative domain is composed by approximately 90 amino acids, containing 8 to 10 cysteines that form internal disulfide bonds. PP1 has two such cysteine-rich domains. Another distinctive feature for most of this family member is that they have a glycosylphosphatidyinositol (GPI) linkage site in the COOH-terminus, and attach to the cell surface by this site. Result of data base search revealed homology of PP1 to other members of uPAR/CD59/Ly-6/snake toxin family. A potential signal sequence is located at the N-terminus, and a hydrophobic domain at the C-terminus matches the consensus for a GPI-anchor, suggesting that PP1, like uPAR, CD59, Ly-6 and Lynx1 is a GPI-linked cell surface molecule.

In order to examine the genomic organization of PP1, we isolated a genomic clone encoding the proximal part of PP1. From a lambda-phage mouse genomic DNA library, a 5.6 kb Sac I genomic DNA fragment containing the 5" region of the PP1 gene was isolated and cloned into plasmid for sequencing. This DNA contains 4 exons and covers approximately ¾ths of the open reading frame described above (provided in SEQ ID NO:3). As with other members of this family, the signal sequence is divided between two exons. Success in sequencing the entire PP1 gene has provided the genetic information for developing PP1 knockout mice.

Expression of PP1: The initial screening indicated that PP1 was expressed in the IFN-γ transgenic pancreas as a 2 kb mRNA, but not the L-4 transgenic pancreas or normal pancreas. Additional Northern blot analysis indicated that a low level of expression of PP1 transcript was present in the heart and liver, and a trace amount in lung was also detected. Two hybridizable species are present in these organs, corresponding to 2 kb and 1.1 kb, respectively. The relatedness of these two transcripts is not known.

To determine the cellular expression of PP1, in situ hybridization analysis was first performed. Hybridization with the antisense RNA for PP1 showed that PP1 transcript restricted in the ducts of regenerating pancreas, and interestingly, the most intense hybridization is present in the region of endocrine cell differentiation, where islets are budding from the ducts. No detectable signal was observed in the normal pancreas. Furthermore, expression was found in the gut endoderm, focally in the stomach and duodenum in embryo at day 15. Notably, PP1 expression was not observed in the fetal developing pancreas at that time. In adult tissue, strong expression of PP1 was also found in epithelium of adult stomach, but again, not in the pancreas.

Cells that expressed PP1 were isolated from embryonic gut from β-gal expressing ROSA 26 mice. These cells were then reintroduced i.v. into the g-IFN mice. After three weeks, pancreatic duct cells of the donor type could be seen, demonstrating the important role of PP1 in pancreatic and gut development.

In a second line of experiments, polyclonal antisera to PP1 was produced for use in immunohistochemical experiments. Rabbits were challenged with a cultured rabbit corneal cell line (SIRC cells) transduced to express the mouse PP1 cDNA. Polyclonal antibody against PP1 was generated and treated with normal SIRC cells to adsorb irrelevant specificities before immunostaining. Immunostaining with PP1 antiserum revealed that PP1 protein is present on the regenerating ducts of pancreas in INF-γ transgenic mice, confirming the above finding by in situ hybridization that only regenerating pancreatic ducts express PP1. In sections on embryo days 14 and 15, the expression appeared at low levels in the epithelium of stomach and intestine. Striking immunoreactivity for PP1 was also found in the epithelium of adult stomach.

In IFN-γ transgenic mice, the newly formed islets bud into the lumen of the ducts where they are protected from infiltration and destruction. These findings indicate that islet stem cells responsible for islet regrowth exist in the regenerating pancreas. The mechanism of INF-γ inducibility in regenerating pancreas is unclear. In addition to INF-γ, several other factors have been investigated during development and growth of pancreas. Keratinocyte growth factor (KGF) is a member of fibroblast growth factor family, which has a mitogenic capacity on epithelia cells. Study of KGF transgenic mice demonstrated that KGF could lead to proliferation of pancreatic duct cells and hepatocyte-like cell within islets, which probably derived from stem cells (Krakowski, 1999). These morphologic changes in the pancreas became more severe after the introduction of epidermal growth factor (EFG) gene into KGF transgenic mice. EGF treatment alone in pigs induced proliferation of pancreatic duct cells and hyperplasia of interlobular ducts. Pancreatic abnormalities have also been reported in transgenic mice expressing tumor growth factor-β (TGF-β) in the islets. Such mice display pancreatic metaplasia and pancreatic tubular complex containing dividing duct cells.

The studies described herein reveal that PP1 expression is up-regulated in INFY transgenic pancreas. It is interesting to note that IFN-γ can up-regulate some uPAR/CD59/Ly-6/snake toxin family protein expression in distinct cell types, e.g. uPAR expression in monocytes; Ly-6A/F and Ly-6C on T cells; and CD59 on tumor cells.

Pancreatic islets develop from epithelium of primitive pancreatic ducts. Recent studies have demonstrated that its development depends on the transcription factor signals such as Pdx1 and Shh. Expression of Pdx1 is first detected in the gut endoderm in E8.5, and later in pancreatic buds where Pdx1-exporessing stem cells develop into differentiated ducts and islets. In adulthood, its expression is limited in pancreatic islets, stomach and duodenum. Lack of Pdx1 leads to arrest of pancreas development at early stage, whereas expression of Pdx1 is up-regulated in epithelium of regenerating or proliferating pancreatic duct.

In contrast to Pdx1, Shh is expressed throughout the gut except pancreas, in which instead express Pdx1 during pancreas development. It has been reported that repression of SHH expressed in embryo by cyclopamine, a Shh signaling inhibitor can induce ectopic pancreas growth in stomach and duodenum, and enlargement of islets in pancreas where expression of Pdx1 is detectable. Taken together, the evidence demonstrates that Pdx1 is required for pancreas development, whereas Shh restricts the pancreas morphogenesis by inhibiting the function of Pdx1 gene.

Interestingly, it was found that PP1 is expressed in stomach and duodenum, the same regions where pancreatic heterotopia occurs after repressing Shh with cyclopamine.

The similarity in the expression pattern of PP1 pattern with Pdx1, with the exception of lack of expression of PP1 in the pancreas, leads us to the conclusion that PP1-expressing cells represent pancreatic stem cells or pancreatic precursors that have the potential to develop or differentiate to pancreatic islet cells, as found in the INF-γ transgenic mice. PP1 participates in the early events of pancreatic development, and during pancreatic regeneration from stem cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying mammalian pancreatic progenitor cells, the method comprising:

Contacting a population of mammalian pancreatic or embryonic gut cells with binding members specific for PP1 polypeptide; and detecting those cells that bind to said binding members specific for PP1 polypeptide;

wherein cells that bind to said binding members specific for PP1 polypeptide are identified as pancreatic progenitor cells.

2. The method of claim 1, wherein pancreatic progenitor cells are progenitors for insulin producing beta cells.

3. The method of claim 1, wherein said population of mammalian pancreatic or embryonic gut cells are pancreatic duct cells.

4. The method of claim 1, wherein said population of mammalian pancreatic or embryonic gut cells are from a fetal donor.

5. The method of claim 1, wherein said population of mammalian pancreatic or embryonic gut cells are from a neonatal donor.

6. The method of claim 1, wherein said population of mammalian pancreatic or embryonic gut cells are from an adult donor.

7. The method of claim 1, wherein said detecting step comprises detection of a label by flow cytometry.

8. The method of claim 1, further comprising the step of:

separating the cells in said population of mammalian pancreatic cells based on binding to said binding members specific for PP1 polypeptide to provide a purified population of pancreatic progenitor cells.

* * * * *